(12) United States Patent
Choi

(10) Patent No.: US 7,503,904 B2
(45) Date of Patent: Mar. 17, 2009

(54) DUAL BALLOON TELESCOPING GUIDING CATHETER

(75) Inventor: Steven B. Choi, Mountain View, CA (US)

(73) Assignee: Cardiac Pacemakers, Inc., St. Paul, MN (US)

(*) Notice: Subject to any disclaimer, the term of this patent is extended or adjusted under 35 U.S.C. 154(b) by 184 days.

(21) Appl. No.: 10/132,093

(22) Filed: Apr. 25, 2002

(65) Prior Publication Data

US 2003/0204138 A1    Oct. 30, 2003

(51) Int. Cl.
A61M 29/00 (2006.01)
A61M 25/00 (2006.01)
A61B 6/00 (2006.01)

(52) U.S. Cl. .................. 604/101.01; 604/103.07; 600/434

(58) Field of Classification Search .............. 600/433, 600/434, 435; 604/101.01, 101.02, 101.03, 604/101.05, 103.06, 103.07, 103.08; 606/108, 606/191, 192, 194, 198

See application file for complete search history.

(56) References Cited

U.S. PATENT DOCUMENTS

| | | | |
|---|---|---|---|
| 5,000,743 A * | 3/1991 | Patel ....................... 606/194 |
| 5,087,246 A * | 2/1992 | Smith ................... 604/103.13 |
| 5,179,961 A | 1/1993 | Littleford et al. |
| 5,250,070 A * | 10/1993 | Parodi ..................... 606/194 |
| 5,571,161 A | 11/1996 | Starksen |
| 5,765,568 A | 6/1998 | Sweezer, Jr. et al. |
| 5,775,327 A | 7/1998 | Randolph et al. |
| 5,792,300 A * | 8/1998 | Inderbitzen et al. .... 156/244.13 |
| 5,795,325 A | 8/1998 | Valley et al. |
| 5,814,016 A * | 9/1998 | Valley et al. ............. 604/96.01 |
| 5,833,650 A * | 11/1998 | Imran ....................... 604/509 |
| 6,021,340 A | 2/2000 | Randolph et al. |
| 6,029,671 A * | 2/2000 | Stevens et al. ............. 128/898 |
| 6,122,552 A | 9/2000 | Tockman et al. |
| 6,126,635 A | 10/2000 | Simpson et al. |
| 6,156,053 A * | 12/2000 | Gandhi et al. ............. 606/194 |
| 6,190,357 B1 | 2/2001 | Ferrari et al. |
| 6,287,319 B1 | 9/2001 | Aboul-Hosn et al. |
| 6,290,697 B1 | 9/2001 | Tu et al. |
| 6,416,511 B1 | 7/2002 | Lesh et al. |
| 6,533,767 B2 | 3/2003 | Johansson et al. |
| 6,540,712 B1 | 4/2003 | Parodi et al. |
| 6,623,471 B1 | 9/2003 | Barbut |
| 6,626,886 B1 | 9/2003 | Barbut |
| 6,635,196 B1 * | 10/2003 | Goggins ..................... 264/1.7 |
| 6,638,268 B2 * | 10/2003 | Niazi ........................ 604/528 |
| 2001/0047138 A1 * | 11/2001 | Kokate et al. .............. 600/585 |
| 2002/0059827 A1 * | 5/2002 | Smith ...................... 73/204.26 |
| 2002/0087119 A1 * | 7/2002 | Parodi .................. 604/103.07 |
| 2002/0156417 A1 * | 10/2002 | Rich et al. .................... 604/65 |
| 2003/0023227 A1 | 1/2003 | Zadno-Azizi et al. |
| 2003/0055378 A1 * | 3/2003 | Wang et al. ............ 604/103.07 |

* cited by examiner

Primary Examiner—Max Hindenburg
Assistant Examiner—Jonathan M Foreman
(74) Attorney, Agent, or Firm—Hollingsworth & Funk, LLC

(57) ABSTRACT

A guiding catheter includes an inner guide movably disposed within an outer guide. Both inner and outer guides include inner and outer balloons, respectively, located at the distal tip of the guides. The inner guide balloon is fluted, thereby allowing blood to flow past the implanted balloon when inflated. The outer balloon is substantially annular in shape and is deployable as an occlusion balloon. Various sensors can be provided at the distal end of the guiding catheter to assist in locating a destination vessel or structure of interest.

42 Claims, 5 Drawing Sheets

Section 1-1

Section 2-2

DUAL BALLOON TELESCOPING GUIDING CATHETER

FIELD OF THE INVENTION

The invention relates generally to surgical catheters, and more particularly to guiding catheters using balloons affixed to the distal tips of telescoping inner and outer guides.

BACKGROUND OF THE INVENTION

Catheters are used in a variety of medical procedures. In some applications, these devices provide physicians the ability to explore, operate, and insert drugs/medical devices in various reaches of the anatomy without invasive surgery. Oftentimes, the catheters have medical devices mounted on the catheter shaft. For example, an electrophysiological (EP) ablation catheter has an ablation electrode mounted at a distal tip of the catheter. In another application, guiding catheters are used to create an easily navigable pathway to be used for delivery of various payloads such as drugs, therapeutic/diagnostic devices (e.g., EP mapping and ablation electrodes), and implantable devices (e.g., cardiac pacing/defibrillation leads).

Guiding catheter systems are typically configured with a profile that is optimized for the intended method of access. For example, when trying to access the coronary sinus of a patient's heart, one method is to enter the venous system through an incision at a large vein such as the subclavian vein near the shoulder. A guiding catheter is inserted through this incision and is sent in an arced path through the superior vena cava into the right atrium of the heart. From the right atrium, the ostium of the coronary sinus must be located. A catheter with a distal contour including a relatively sharp bend will point the catheter towards the likely location of the coronary sinus once the right atrium is reached. The contours of pre-shaped guiding catheters are often fixed during manufacture.

A pre-shaped guiding catheter is sometimes used to blindly locate the coronary sinus ostium. This endeavor, however, is complicated by the fact that the location of the coronary sinus ostium may vary appreciably from one patient to another, especially among patients with diseased hearts. If the pre-shaped catheter is introduced and found to be not well adapted to the patient's anatomy, the catheter must be removed and a replaced with a catheter having a different shape. Replacing a catheter in this manner is time consuming, expensive, and can cause unnecessary trauma to the patient.

Even when the catheter has an ideal shape for a given application, the size and flexibility of the catheter that provides maneuverability through a convoluted access path becomes a disadvantage when trying to manipulate the distal end of the catheter in the right atrium. Further, once the catheter has cannulated the destination vessel, the flexible distal tip may be dislodged from the destination vessel due to shape distortions caused by introducing a payload through the catheter.

The primary objective of a typical guiding catheter procedure is to locate and cannulate a vessel of interest in the least amount of time. Finding and cannulating the coronary sinus, for example, can become a time consuming, trial and error procedure even in a healthy patient. Patients exhibiting symptoms of advanced heart disease can have blockages or deformations of heart structure, further complicating the task of locating the ostium of the coronary sinus.

There is a need for an improved guiding catheter that provides for more efficient access to vessels of interest, such as the coronary sinus. There is a further need for a catheter that can be positively secured in a cannulated destination vessel. The present invention fulfills these and other needs, and addresses other deficiencies of prior art implementations and techniques.

SUMMARY OF THE INVENTION

The invention relates to a guiding catheter for use in accessing various anatomical regions, particularly the heart. In particular, a guiding catheter of the present invention employs a telescopic arrangement of inner and outer guides, with each guide provided with a controllably inflatable balloon.

According to one embodiment, a guiding catheter of the present invention includes an outer guide having a pre-formed distal curve, a guide lumen, and an inflation lumen. The guiding catheter also includes an inner guide movably disposed within the guide lumen of the outer guide. The inner guide includes an inflation lumen and can further include a pre-formed distal curve. An annular balloon is fixably mounted to a distal end of the outer guide and in fluid connection with the inflation lumen of the outer guide. A fluted balloon is fixably mounted to a distal end of the inner guide and in fluid connection with the inflation lumen of the inner guide. At least two inflation mechanisms are provided, each independently in fluid connection with the inflation lumens of the inner and outer guides. The inflation mechanisms are used to selectively pressurize and depressurize a fluid within the inflation lumens to respectively inflate and deflate the annular and fluted balloons.

One or more sensors can be provided at a distal end of the guiding catheter to assist in locating a destination vessel or structure of interest. A sensor can be mounted to the outer guide, the inner guide, or both the outer and inner guides. Useful sensor arrangements can include one or more of an optical sensor, infrared sensor, ultrasound sensor, pressure sensor, temperature sensor, flow sensor, and oxygen sensor.

According to another embodiment, a method for accessing a destination vessel in a patient's heart according to the present invention involves introducing a distal end of a guiding catheter into a patient's access vessel. The guiding catheter according to this embodiment includes an outer guide having a guide lumen and an annular balloon mounted to a distal end of the outer guide. The guiding catheter further includes an inner guide movably disposed within the guide lumen of the outer guide. The inner guide includes a fluted balloon mounted to a distal end of the inner guide.

The method further involves advancing the distal end of the guiding catheter through a circulatory pathway, and distally extending the inner guide to engage the destination vessel with the distal end of the inner guide. The inner guide is distally extended to seat the inner guide in the destination vessel. The fluted balloon is inflated to anchor the inner guide in the destination vessel.

According to a further aspect, after engaging the destination vessel with the inner guide, the outer guide is distally advanced over the inner guide to engage the destination vessel with the outer guide. The annular balloon is inflated to occlude blood flow. A contrast media is injected into the guiding catheter for mapping blood vessels. Various types of sensing can be employed at the distal end of the guiding catheter to assist in locating a destination vessel or structure of interest.

The above summary of the present invention is not intended to describe each embodiment or every implementation of the present invention. Advantages and attainments, together with a more complete understanding of the invention, will become apparent and appreciated by referring to the

Figure 1:
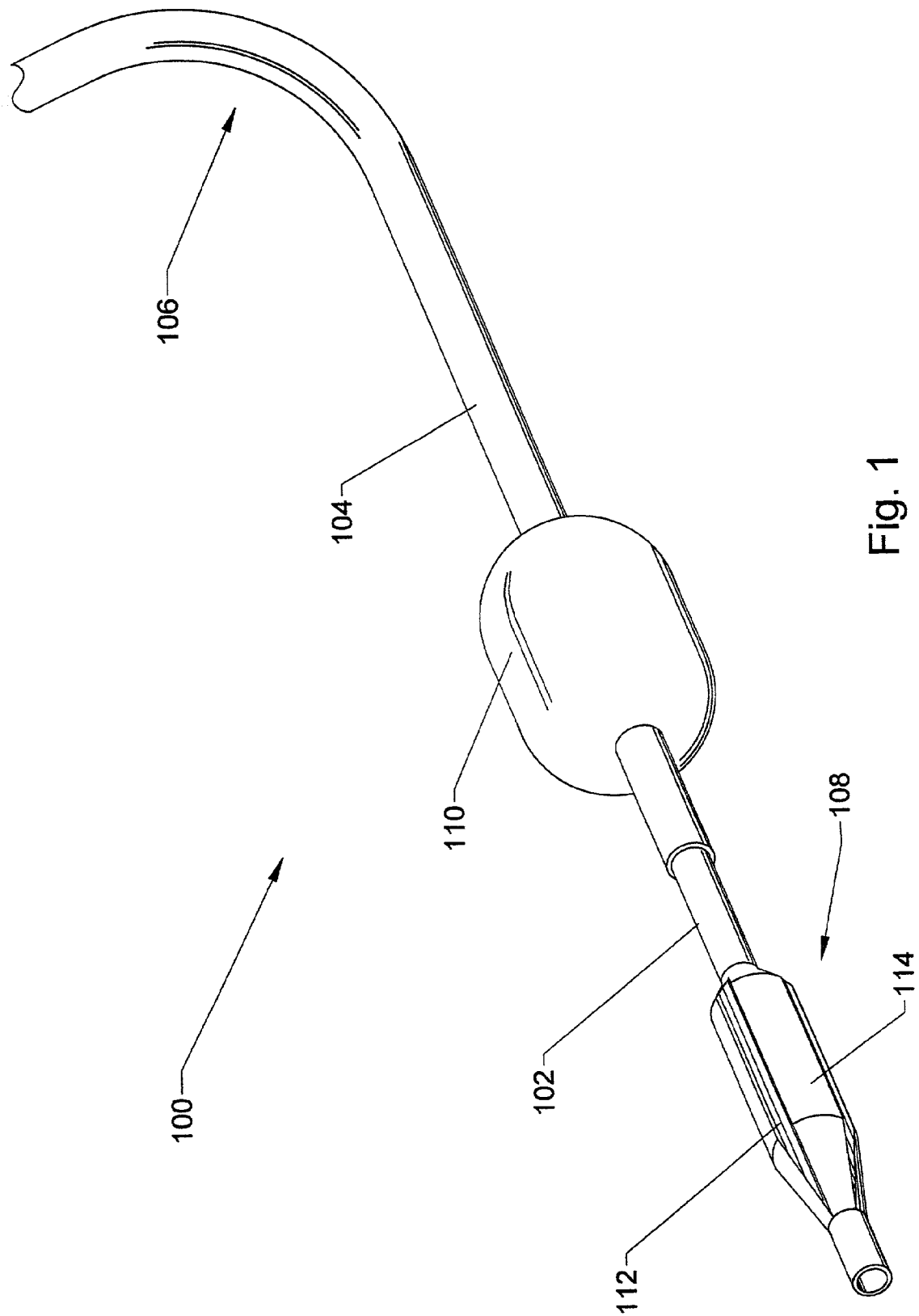
FIG. 1 is a perspective view of a catheter according to an embodiment of the present invention.

While the invention is amenable to various modifications and alternative forms, specifics thereof have been shown by way of example in the drawings and will be described in detail herein. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings which form a part hereof, and in which is shown by way of illustration, various embodiments in which the invention may be practiced. It is to be understood that other embodiments may be utilized, and structural and functional changes may be made without departing from the scope of the present invention.

In FIG. 1, a catheter according to the present invention, generally indicated by reference numeral 100, is illustrated. The catheter 100 utilizes a telescoping guide configuration that includes an inner guide 102 movably disposed within an outer guide 104. The outer guide 104 has a pre-formed curve 106 near a distal end. The pre-formed curve 106 typically includes a shape optimized for the intended access path and destination vessel. Fluted and annular balloons 108, 110 are fixably mounted to the inner and outer guides 102, 104, respectively.

The fluted balloon 108 includes fluted grooves 112 adjacent to inflatable sections 114. The fluted balloon 108 is inflated via an inflation lumen within the inner guide 102. The fluted balloon 108 is configured such that the inflatable sections 114 are enlarged upon inflation, the enlarged inflatable sections 114 gripping an interior surface of a blood vessel. The fluted grooves 112 allow some blood to flow past the inflated balloon 108, thereby preventing complete occlusion of the blood vessel. In this way, the fluted balloon 108 can advantageously be used to secure the distal tip of the inner guide 102 for a relatively long period of time without introducing problems caused by full blood flow occlusion.

The fluted balloon 108 may be formed similar to a standard latex occlusion balloon, with the additional application of longitudinal adhesive sections to the inside of the balloon 108. The adhesive sections bond an outer, inflatable member of the balloon 108 to the guide 102 to form the fluted grooves 112. The adhesive sections prevent an area encompassed by the fluted grooves 112 from inflating when pressurizing the balloon 108. The areas between adhesive sections serve as the inflatable sections 114.

An alternate configuration of the fluted balloon 108 may include bonding a plurality of elongated balloon sections lengthwise along the inner guide 102, each balloon section forming an inflatable section 114. The spaces between balloon sections form the fluted grooves 112. The elongated balloons can include a common fluid connection for inflation, such as a ring shaped manifold.

The outer guide balloon 110 (i.e., annular balloon) can be constructed similarly to occlusion balloons known in the art. The annular balloon 110 is controllably expandable to substantially block the vessel in which the outer guide 104 is located, thereby occluding blood flow in the vessel. For both balloons 108, 110, a fluid such as saline solution is typically used to provide inflation pressure.

The inner and outer guides 102, 104 can be constructed using a variety of techniques known in the art. The guides 102, 104 can be formed of an extruded polymer, such as Pebax thermoplastic elastomer resin. Other polymer materials, such as nylon and polyurethane, are also commonly used for catheter guides. The guides 102, 104 may include regions of different material stiffness (e.g., durometer rating) to provide customized performance. In a typical application, distal regions of the guides 102, 104 are fabricated to be relatively flexible, thereby allowing maneuverability through convoluted paths. A proximal region of the guides 102, 104 is made stiffer than the distal region, providing kink resistance and enhanced transmission of axial forces and torque.

As shown in FIG. 1, the pre-formed curve 106 is typically located proximal to the annular balloon 110. Various curve shapes are possible, the shapes being dictated by the destination vessel and access path of interest. The pre-formed curve 106 is made flexible such that the outer guide 104 straightens while being guided through the vasculature, yet resumes the pre-formed shape when a wider cavity, such as a heart chamber, is reached.

Figure 2:
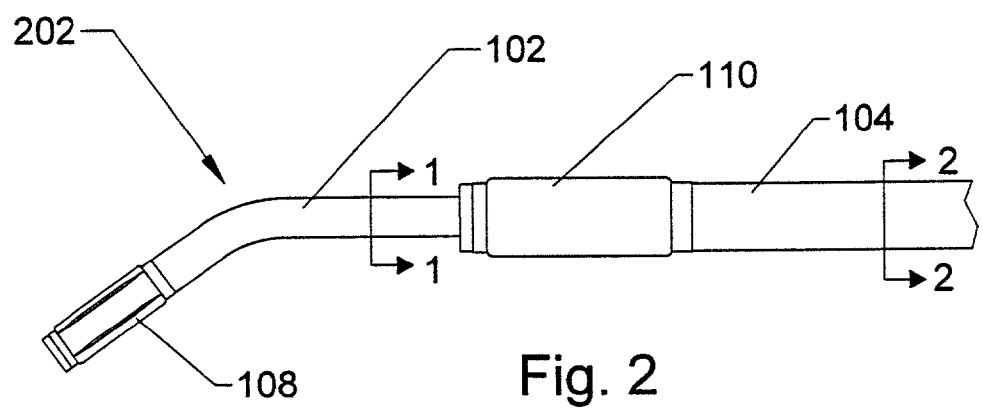
FIG. 2 is a side view of a distal end of the catheter according to an embodiment of the present invention.

The inner guide 102 may also include a pre-formed shape 202 at a distal end, as seen in FIG. 2. The inner guide 102 can be made retractable within the outer guide 104 such that the inner guide's distal end substantially takes the shape of the outer guide 104 when retracted. When the inner guide 102 is extended such that the pre-formed curve 202 extends beyond the outer guide's distal tip, the pre-formed curve 202 resumes its original, pre-formed shape.

The pre-formed curves 106, 202 can be thermoset on the guides 102, 104 in production. If the guide material does not take a thermoset, a jacket of thermoset or otherwise pre-formed material can be enclosed around a distal end of the guides 102, 104. The jacket causes the pre-formed curve 106, 202 to conform to a desired shape.

Figure 3:
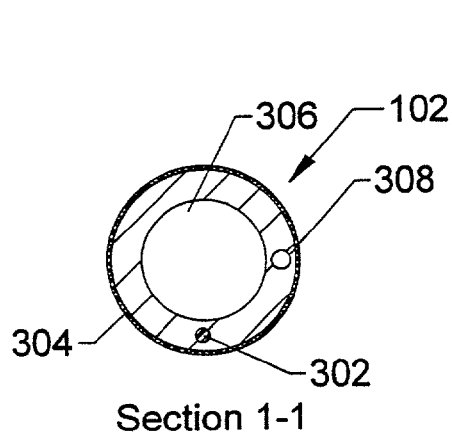
FIG. 3 is a cross sectional view of an inner guide corresponding to section 11 in FIG. 2.
Figure 4:
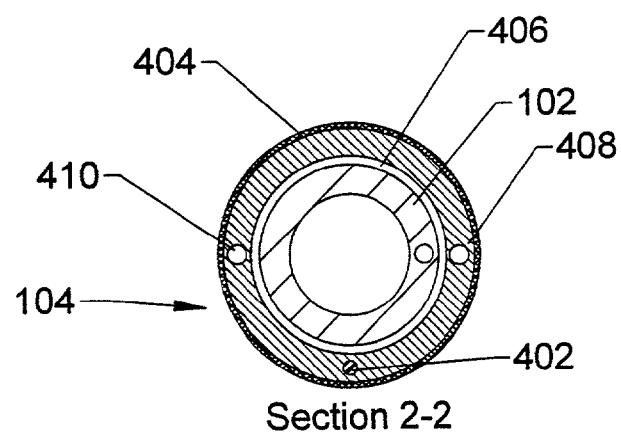
FIG. 4 is a cross sectional view of an outer guide corresponding to section 2-2 in FIG. 2.

Alternatively, a stylet 302, 402, best seen in FIGS. 3 and 4, made of Nitonol or other superelastic material can be affixed (e.g., bonded or enclosed) within a distal portion of one or both of the guides 102, 104. The superelastic properties of the stylet 302, 402 allow it to be substantially deformed, thereby allowing the distal end to be straightened for guiding through veins and/or arteries, then returning to the preformed shape when a desired access point is reached.

Figure 5:
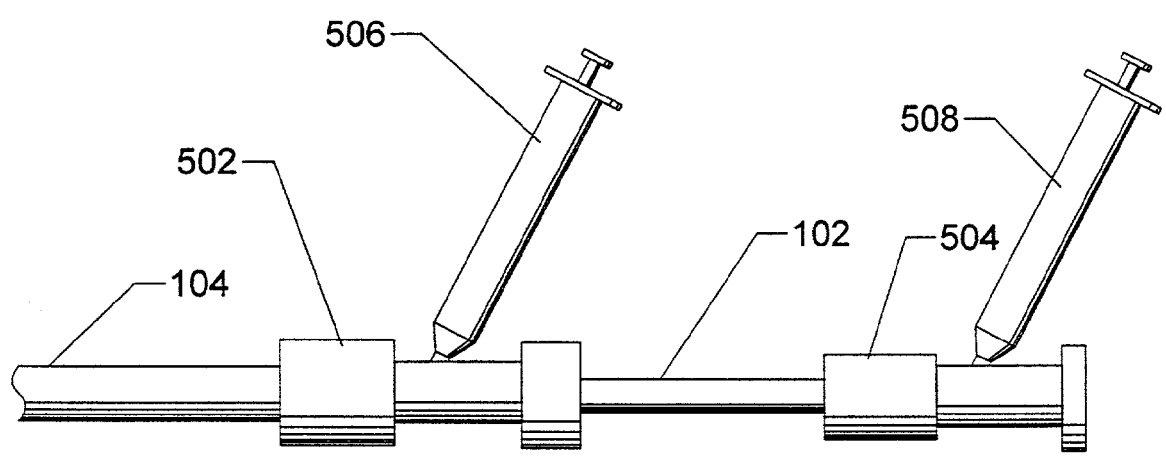
FIG. 5 is a perspective view of the distal end of the outer guide according to an embodiment of the present invention.

The guides 102, 104 may each include a braid 304, 404 as seen in FIGS. 4 and 5. The braids 304, 404 are typically formed of fine stainless steel wires, although stainless steel ribbon and/or artificial fibers can also be used to form the braids 304, 404. The braids 304, 404 may cover all or part of the guides 102, 104, improving axial stiffness and kink resistance therein with only a minimal reduction in maneuvering flexibility. The braids 304, 404 can be bonded or otherwise affixed to an exterior surface of the guides 102, 104. Alternatively, the braids 304, 404 can be molded within the walls of the guides 102, 104.

The inner and outer guides 102, 104 typically include guide lumens 306, 406. The outer guide lumen 406 is open throughout the length of the outer guide 104. The inner guide lumen 306 is typically open for guiding applications, although an open inner guide lumen 306 may not be required if the inner guide 102 is not used to carry a payload. A lubricious liner made from a material such as PTFE can be applied to an interior surface of the lumens 306, 406 to enhance passage of payloads therethrough and movement of the inner guide 102 within the outer guide 104.

The inner and outer guides 102, 104 contain additional lumens. The guides 102, 104 at least contain inflation lumens 308, 408 that are in fluid connection with the distal balloons 108, 110. The inflation lumens 308, 408 communicate a pressurized fluid from a proximal end to the distal end of the guides 102, 104. The fluid is introduced at a proximal end of the guides 102, 104 and used for inflating the balloons 108, 110. A fluid connection between inflation lumens 308, 408 and balloons 108, 110 can be created by forming an orifice through each outer wall of the guides 102, 104 into the lumens 308, 408. The balloons 108, 110 in such a configuration each have an inflation opening, the opening being positioned over the orifice when the balloons 108, 110 are attached to the guides 102, 104.

FIG. 5 illustrates proximal inflation mechanisms for the inner and outer guides 102, 104. The proximal end of the guides 102, 104 are fitted with valves 502, 504 (e.g., hemostatic valves). The valves 502, 504 provide a fluid seal for the guide lumens 306, 406, thereby helping to prevent the catheter 100 from introducing an air embolism in the blood vessels. The valve 502 seals the inner guide 102 within the outer guide 104. The valve 504 seals any payloads that may be introduced through the inner guide lumen 306.

The valves 502, 504 also provide fluid connections between the inflation lumens 308, 408 and proximal inflation mechanisms 506, 508. The proximal inflation mechanisms 506, 508 may include a syringe or pump. The inflation mechanisms 506, 508 may also include one or more pressure gauges to monitor the fluid inflation pressure.

Turning back to FIG. 4, an accessory lumen 410 is shown in the outer guide 104. The accessory lumen 410 is preferably extruded into the wall of the outer guide 104. The accessory lumen 410 can be used for carrying accessory payloads such as injections and guide wires. The accessory lumen 410 can also be used to carry conductors or other communication media coupled to a sensor attached to the outer guide's distal end.

Figure 6:
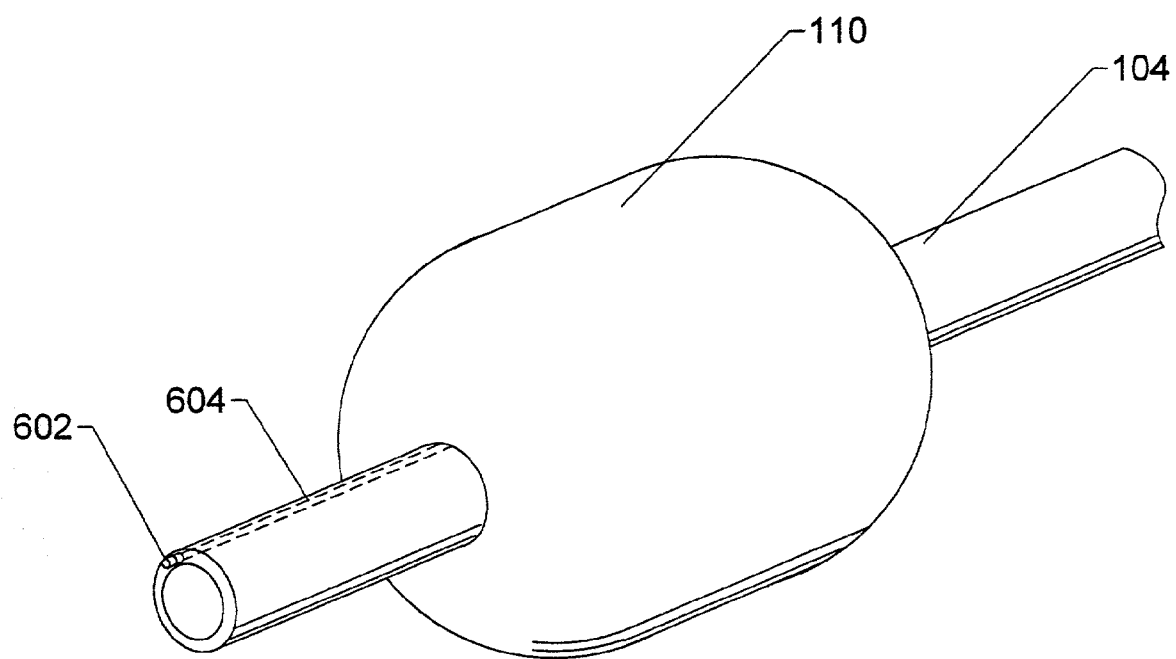
FIG. 6 is a side view of proximal inflation mechanisms according to the present invention.

Referring now to FIG. 6, an exemplary sensor configuration is illustrated on an outer guide 104. The sensor 602 can include a sensor/transducer that measures pressure, temperature, flow, oxygen, infrared, and ultrasound. Miniature sensor assemblies are available in the form of Micro-Electro-Mechanical Systems (MEMS) that are particularly suited to this application. Such MEMS sensors/transducers are commercially available and adaptable to medical devices. A communication medium 604 is coupled to the sensor 602 and communicates sensor signals to measuring/processing equipment at the proximal end of the catheter 100. The communication medium 604 typically includes at least one electrical conductor and can be disposed within the accessory lumen 410 of the outer guide 104.

An alternate sensor 602 includes a fiber optical sensor (e.g., lens) for such applications as thermal, visual, or laser-Doppler velocimetry sensing. The communication medium 604 in an optical sensor includes an optical fiber that can be disposed within the accessory lumen 410. It is understood that a similar sensor and communication medium arrangement can be provided for the inner guide 102, exclusive of, or in addition to, such an arrangement provided for the outer guide 104.

A catheter 100 according to the present invention has features particularly useful in accessing anatomical features within the heart. An exemplary use of the catheter 100 is described hereinbelow relating to accessing the coronary sinus, it being understood that other vessels of interest can be similarly accessed in accordance with the principles of the present invention. Coronary sinus access is often required in pacing/defibrillation lead implant procedures. Since the opening (ostium) of the coronary sinus into the right atrium is relatively small compared to the size of the right atrium, the coronary sinus is a challenging target vessel for cannulation.

Figure 7:
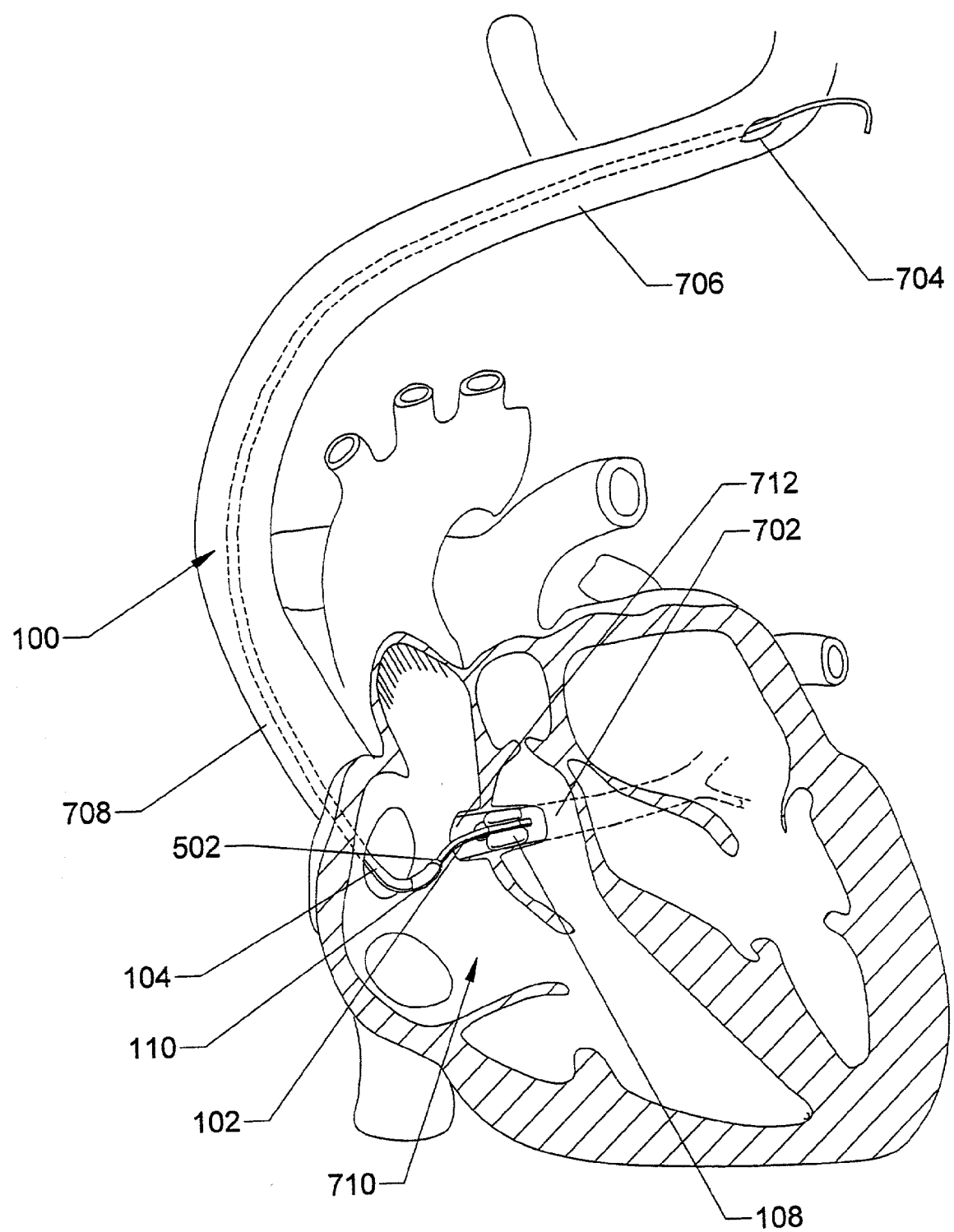
FIG. 7 is a perspective cutaway view of a heart, illustrating a catheter according to the present invention cannulating the coronary sinus.

Aspects of a coronary sinus access procedure are shown in FIG. 7. Catheterizing the coronary sinus 702 involves introducing the distal tip of the catheter 100 through an incision 704 into a percutaneous access vessel 706. Common access vessels include the right cephalic vein and the subclavian vein. The catheter 100 is advanced through access vessel 706 into the superior vena cava 708, thereby entering into the right atrium 710. From the right atrium 710, the catheter 100 can then locate the coronary sinus ostium 712, thereby readying the catheter 100 for introduction into the coronary sinus 702.

The clinician may utilize a sensor 602 in the outer guide 104 to assist in locating the coronary sinus ostium 712. For example, a flow sensor or Doppler sensor can sense the stream of blood exiting the coronary sinus based on flow rate or flow velocity. A thermal or infrared sensor can look for a higher temperature region indicative of the typically higher temperature blood leaving the coronary sinus 702. Other devices, such as a fiber optic camera or ultrasound transducer, can provide a visual representation of the heart structure to aid in guiding the catheter 100.

The catheter 100 can be maneuvered by extending and/or torquing a proximal end of the outer guide 104, thereby directing the guide's pre-formed distal end 106. The inner guide 102 can also be extended and torqued to probe for the ostium at a distal end. By using the sensor 602 and/or other means of visualizing the catheter 100 (e.g., angiography/venography), a distal tip of the inner or outer guides 102, 104 can be maneuvered to engage the ostium.

The outer guide 104 may include an accessory lumen 410 (as shown in FIG. 4) that can accept a probing wire. The probing wire can be extended through the outer guide 104 to assist in locating the ostium. The probing wire can include a distal curve that assumes a pre-set shape upon extension from the outer guide 104, thereby providing an alternate shape to search for the ostium.

After the ostium is located, the outer guide 104 may be inserted into the ostium. Alternatively, the inner guide 102 may be extended from the outer guide 104 into the ostium, thereby providing an extension of the outer guide 104. Once the coronary sinus is cannulated, the outer guide 104 may be distally extended so that the annular balloon 110 is enclosed within the coronary sinus. The annular balloon 110 can then be inflated to provide occlusion for a contrast injection. The contrast injection can be introduced through the inner or outer guides 102, 104, and is used for mapping branches of the coronary sinus (e.g., venography/angiography), typically identifying a branch in which to wedge a pacing/defibrillation lead.

After the contrast mapping is complete, the inner guide 102 is advanced into position, the outer guide 104 is at least partially retracted, and the fluted balloon 108 is inflated. As seen in FIG. 7, the inflated fluted balloon 108 secures the inner guide 102 within the coronary sinus so as to prevent dislodgment, while advantageously allowing perfusion of blood through the coronary sinus. After securing the inner guide 102, a payload can be introduced through the inner guide lumen 306 and into the coronary sinus 702. After delivery of the payload (e.g., a pacing or defibrillation lead implanted at a desired location), the catheter 100 is properly retracted and removed from the patient's body.

It will, of course, be understood that various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. A guiding catheter, comprising:
   an outer guide configured to navigate into the coronary sinus, the outer guide comprising a pre-formed distal curve configured to facilitate cannulation of the coronary sinus from the superior vena cava through the right ventricle by the outer guide, a guide lumen, an accessory lumen, a sensor, a distal region flexible relative to a proximal region, and an inflation lumen, the guide lumen of the outer guide dimensioned to receive an implantable cardiac lead and the sensor positioned at a distal end of the outer guide;
   an inner guide movably disposed within the guide lumen of the outer guide, the inner guide comprising an inflation lumen, a distal region flexible relative to a proximal region, a stylet enclosed within a distal portion of the inner guide, and a pre-formed curve on a distal end of the inner guide, the distal end of the inner guide having a circumference, the inner and outer guides each configured such that the pre-formed curve of the inner guide substantially takes the shape of the outer guide when the pre-formed curve of the inner guide is retracted within the outer guide and the pre-formed curve of the inner guide assumes its pre-formed shape when extended beyond the distal end of the outer guide;
   an annular balloon fixably mounted on the outer guide distal of the pre-formed distal curve of the outer guide and in fluid connection with the inflation lumen of the outer guide, the annular balloon configured to seal the coronary sinus and anchor the inner guide in the coronary sinus in an inflated configuration by engagement with the coronary sinus;
   a fluted balloon fixably mounted around the entirety of the circumference of the inner guide distal of the pre-formed bend, the fluted balloon in fluid connection with the inflation lumen of the inner guide, the fluted balloon comprising a plurality of flutes arranged generally parallel to a longitudinal axis of the inner guide and configured to retain a fluted configuration sufficient to permit perfusion of fluid flow relative to the fluted balloon when pressurized; and
   at least two inflation mechanisms each independently in fluid connection with the inflation lumens of the inner and outer guides, the inflation mechanisms pressurizing and depressurizing a fluid within the inflation lumens to respectively inflate and deflate the annular and fluted balloons.

2. A guiding catheter according to claim 1, wherein the accessory lumen of the outer guide is adapted to receive a contrast fluid injection.

3. A guiding catheter according to claim 1, wherein the accessory lumen of the outer guide is adapted to receive a probing wire.

4. A guiding catheter according to claim 1, wherein the sensor comprises at least one fiber optic filament, the at least one fiber optic filament disposed within the accessory lumen and allowing visualization at the distal tip of the outer guide.

5. A guiding catheter according to claim 1, further comprising at least one electrical conductor disposed within the accessory lumen and coupled to the sensor.

6. A guiding catheter according to claim 1, wherein the sensor comprises an infrared sensor.

7. A guiding catheter according to claim 1, wherein the sensor comprises an ultrasound sensor.

8. A guiding catheter according to claim 1, wherein the sensor comprises a pressure sensor.

9. A guiding catheter according to claim 1, wherein the sensor comprises a flow sensor.

10. A guiding catheter according to claim 1, wherein the sensor comprises a temperature sensor.

11. A guiding catheter according to claim 1, wherein the sensor comprises an oxygen sensor.

12. A guiding catheter according to claim 1, wherein the inner guide further comprises a guide lumen, the inner guide lumen dimensioned to receive the implantable cardiac lead.

13. A guiding catheter according to claim 12, wherein the guide lumen of the inner guide is dimensioned to receive an implantable pacing lead.

14. A guiding catheter according to claim 12, wherein the guide lumen of the inner guide is dimensioned to receive an implantable defibrillation lead.

15. A guiding catheter according to claim 1, wherein the guide lumen of the outer guide is dimensioned to receive an implantable pacing lead.

16. A guiding catheter according to claim 1, wherein the guide lumen of the outer guide is dimensioned to receive an implantable defibrillation lead.

17. A guiding catheter according to claim 1, wherein the fluted balloon comprises a plurality of balloon sections arrayed around the circumference of the inner guide and respectively bonded to an outer surface of the inner guide, each of the plurality of flutes being formed between adjacent balloon sections.

18. A guiding catheter according to claim 1, wherein each of the flutes of the fluted balloon correspond to respective longitudinal balloon-internal sections of the fluted balloon bonded to an outer surface of the inner guide.

19. A guiding catheter according to claim 1, further comprising braiding affixed to an exterior surface of the outer guide.

20. A guiding catheter according to claim 1, further comprising a polytetrafluoroethylene liner within the guide lumen of the outer guide.

21. A guiding catheter, comprising:
   an outer guide configured to navigate into the coronary sinus, the outer guide comprising a guide lumen, an accessory lumen, a sensor, a distal region flexible relative to a proximal region, and an inflation lumen, the guide lumen of the outer guide dimensioned to receive an implantable cardiac lead and the sensor positioned at a distal end of the outer guide;
   an inner guide movably disposed within the guide lumen of the outer guide, the inner guide comprising an inflation lumen, a distal region flexible relative to a proximal region, a stylet enclosed within a distal portion of the inner guide, and a pre-formed curve on a distal end of the inner guide, the distal end of the inner guide having a circumference, the inner and outer guides each configured such that the pre-formed curve of the inner guide substantially takes the shape of the outer guide when the pre-formed curve of the inner guide is retracted within the outer guide and the pre-formed curve of the inner guide assumes its pre-formed shape when extended beyond the distal end of the outer guide;

an annular balloon disposed at the distal end of the outer guide and in fluid connection with the inflation lumen of the outer guide, the annular balloon configured to seal the coronary sinus and anchor the inner guide in the coronary sinus in an inflated configuration by engagement with the coronary sinus;

a fluted balloon disposed around the entirety of the circumference of the inner guide distal of the pre-formed bend, the fluted balloon in fluid connection with the inflation lumen of the inner guide, the fluted balloon comprising a plurality of flutes arranged generally parallel to a longitudinal axis of the inner guide and configured to retain a fluted configuration when pressurized; and at least two inflation mechanisms each in fluid connection with the inflation lumens of the inner and outer guides, the inflation mechanisms configured to selectably pressurize and depressurize the annular balloon to control occlusion of fluid flow relative to the annular balloon, and to selectably pressurize and depressurize the fluted balloon to permit perfusion of fluid flow relative to the fluted balloon and control anchoring of the fluted balloon within a cardiac vessel.

22. A guiding catheter according to claim 21, wherein the accessory lumen of the outer guide is adapted to receive a probing wire.

23. A guiding catheter according to claim 21, wherein the sensor comprises at least one fiber optic filament, the at least one fiber optic filament disposed within the accessory lumen and allowing visualization at the distal tip of the outer guide.

24. A guiding catheter according to claim 21, wherein the sensor comprises at least one of an infrared sensor and an ultrasound sensor.

25. A guiding catheter according to claim 21, wherein the sensor comprises at least one of a pressure sensor, a flow sensor, and a temperature sensor.

26. A guiding catheter according to claim 21, wherein the sensor comprises an oxygen sensor.

27. A guiding catheter according to claim 21, wherein the outer guide comprises a pre-formed distal curve.

28. A guiding catheter according to claim 21, wherein the inner guide further comprises a pre-formed distal curve.

29. A guiding catheter according to claim 21, wherein the outer guide comprises a pre-formed distal curve.

30. A guiding catheter according to claim 21, wherein the inner guide further comprises a guide lumen, the inner guide lumen dimensioned to receive the implantable cardiac lead.

31. A guiding catheter according to claim 30, wherein the guide lumen of the inner guide is dimensioned to receive an implantable pacing lead.

32. A guiding catheter according to claim 30, wherein the guide lumen of the inner guide is dimensioned to receive an implantable defibrillation lead.

33. A guiding catheter according to claim 30, further comprising a polytetrafluoroethylene liner within the guide lumen of the inner guide.

34. A guiding catheter according to claim 30, further comprising a polytetrafluoroethylene liner within the guide lumen of the inner guide.

35. A guiding catheter according to claim 21, wherein the guide lumen of the outer guide is dimensioned to receive an implantable pacing lead.

36. A guiding catheter according to claim 21, wherein the guide lumen of the outer guide is dimensioned to receive an implantable defibrillation lead.

37. A guiding catheter of claim 21, wherein the outer guide comprises a pre-formed distal curve proximal of the annular balloon, the pre-formed distal curve configured to facilitate cannulation of the coronary sinus from the superior vena cava through the right ventricle by the outer guide.

38. A guiding catheter according to claim 21, wherein the fluted balloon comprises a plurality of balloon sections arrayed around the circumference of the inner guide and respectively bonded to an outer surface of the inner guide, each of the plurality of flutes being formed between adjacent balloon sections.

39. A guiding catheter according to claim 21, wherein each of the flutes of the fluted balloon correspond to respective longitudinal balloon-internal sections of the fluted balloon bonded to an outer surface of the inner guide.

40. A guiding catheter according to claim 21, further comprising braiding affixed to an exterior surface of the outer guide.

41. A guiding catheter according to claim 21, further comprising a polytetrafluoroethylene liner within the guide lumen of the outer guide.

42. A guiding catheter, comprising:
an outer guide configured to navigate into the coronary sinus, the outer guide comprising a guide lumen, a pre-formed distal curve configured to facilitate cannulation of the coronary sinus from the superior vena cava through the right atrium by the outer guide, a distal region flexible relative to a proximal region, and an inflation lumen, the guide lumen of the outer guide dimensioned to receive an implantable cardiac lead;

an inner guide movably disposed within the guide lumen of the outer guide, the inner guide comprising an inflation lumen, a distal region flexible relative to a proximal region, a stylet enclosed within a distal portion of the inner guide, and a pre-formed curve on a distal end of the inner guide, the distal end of the inner guide having a circumference, the inner and outer guides each configured such that the pre-formed curve of the inner guide substantially takes the shape of the outer guide when the pre-formed curve of the inner guide is retracted within the outer guide and the pre-formed curve of the inner guide assumes its pre-formed shape when extended beyond the distal end of the outer guide;

an annular balloon disposed at the distal end of the outer guide distal of the pre-formed distal curve of the outer guide and in fluid connection with the inflation lumen of the outer guide, the annular balloon configured to seal the coronary sinus and anchor the inner guide in the coronary sinus in an inflated configuration by engagement with the coronary sinus;

a fluted balloon disposed around the entirety of the circumference of the inner guide distal of the pre-formed bend, the fluted balloon in fluid connection with the inflation lumen of the inner guide, the fluted balloon comprising a plurality of flutes arranged generally parallel to a longitudinal axis of the inner guide and configured to retain a fluted configuration when pressurized, each of the flutes of the fluted balloon corresponding to respective longitudinal balloon-internal sections of the fluted balloon bonded to an outer surface of the inner guide; and at least two inflation mechanisms each in fluid connection with the inflation lumens of the inner and outer guides, the inflation mechanisms configured to selectably pressurize and depressurize the annular balloon to control occlusion of fluid flow relative to the annular balloon, and to selectably pressurize and depressurize the fluted balloon to permit perfusion of fluid flow relative to the fluted balloon and control anchoring of the fluted balloon within a cardiac vessel.

* * * * *

UNITED STATES PATENT AND TRADEMARK OFFICE
CERTIFICATE OF CORRECTION

| | | |
|---|---|---|
| PATENT NO. | : 7,503,904 B2 | Page 1 of 1 |
| APPLICATION NO. | : 10/132093 | |
| DATED | : March 17, 2009 | |
| INVENTOR(S) | : Choi | |

It is certified that error appears in the above-identified patent and that said Letters Patent is hereby corrected as shown below:

In the Specification:

Col. 3, line 11: "section 11 in Fig. 2;" should read --section 1-1 in Fig. 2;--.

Signed and Sealed this

Nineteenth Day of May, 2009

JOHN DOLL
*Acting Director of the United States Patent and Trademark Office*